US008265556B2

(12) United States Patent
Tekin et al.

(10) Patent No.: US 8,265,556 B2
(45) Date of Patent: Sep. 11, 2012

(54) INTEGRATED MOBILE PHONE AND MEDICAL IMPLANT MONITORING SYSTEM AND METHOD FOR USING THE SAME

(75) Inventors: Ahmet Tekin, Mission Viejo, CA (US); Suat Utku Ay, Moscow, ID (US); Ahmed Emira, Mission Viejo, CA (US)

(73) Assignee: Waveworks, Inc., Tustin, CA (US)

( * ) Notice: Subject to any disclaimer, the term of this patent is extended or adjusted under 35 U.S.C. 154(b) by 53 days.

(21) Appl. No.: 12/925,581

(22) Filed: Oct. 25, 2010

(65) Prior Publication Data

US 2012/0100887 A1 Apr. 26, 2012

(51) Int. Cl.
*H04B 5/00* (2006.01)
*H04B 1/38* (2006.01)
*A61B 5/07* (2006.01)

(52) U.S. Cl. ........ 455/41.1; 600/302; 455/557; 455/559
(58) Field of Classification Search ............... 604/891.1, 604/502, 93.01, 175, 288.01, 288.04; 455/41.1–41.3, 455/458, 550.1, 552.1, 556.1, 557–559; 600/372–381, 302; 427/527–531; 623/3.11, 623/3.27, 23.16
See application file for complete search history.

(56) References Cited

U.S. PATENT DOCUMENTS

| | | | |
|---|---|---|---|
| 4,625,733 A | 12/1986 | Saynajakangas | |
| 5,948,006 A * | 9/1999 | Mann | 607/61 |
| 6,802,811 B1 | 10/2004 | Slepian | |
| 7,156,809 B2 | 1/2007 | Quy | |
| 7,181,505 B2 | 2/2007 | Haller et al. | |
| 7,265,676 B2 | 9/2007 | Gordon et al. | |
| 7,324,850 B2 | 1/2008 | Persen et al. | |
| 7,395,117 B2 | 7/2008 | Mazar et al. | |
| 7,400,257 B2 | 7/2008 | Rivas | |
| 7,542,878 B2 | 6/2009 | Nanikashvili | |
| 7,584,002 B2 | 9/2009 | Burnes et al. | |
| 7,613,510 B2 | 11/2009 | Rentea et al. | |
| 7,722,536 B2 | 5/2010 | Goodnow | |
| 7,787,946 B2 | 8/2010 | Stahman et al. | |

(Continued)

OTHER PUBLICATIONS

Vidal, N.; López-Villegas, J.M.; , "Changes in Electromagnetic Field Absorption in the Presence of Subcutaneous Implanted Devices: Minimizing Increases in Absorption," *Electromagnetic Compatibility, IEEE Transactions on*, vol. 52, No. 3, pp. 545-555, Aug. 2010.

(Continued)

*Primary Examiner* — Meless N Zewdu
*Assistant Examiner* — William Lu
(74) *Attorney, Agent, or Firm* — Oktay Enterprises Int'l., LLC; Sevgin Oktay

(57) ABSTRACT

Integrated mobile phone and medical implant system. The disclosed system integrates the available electronic resources that already exist in compact and portable devices, such as any generic mobile phone, with a body implantable medical device such that the sensory data obtained from the implant device is transmitted through an electronic umbilical cord directly to the mobile device where the data is analyzed and presented in a user-friendly manner to the user/patient and/or transmitted wirelessly to a remote location for further action, if necessary, without the need for additional equipment. With the switch of software application from a drop-down menu, the mobile device of the system functions both as a normal mobile phone, as a medical monitoring device, or both simultaneously without any interference between the two modes of operations. Method for using the integrated system is also disclosed.

19 Claims, 7 Drawing Sheets

U.S. PATENT DOCUMENTS

| | | | |
|---|---|---|---|
| 2004/0054352 A1* | 3/2004 | Adams et al. | 604/891.1 |
| 2005/0075698 A1* | 4/2005 | Phillips et al. | 607/61 |
| 2005/0113887 A1* | 5/2005 | Bauhahn et al. | 607/61 |
| 2007/0055324 A1* | 3/2007 | Thompson et al. | 607/60 |
| 2007/0233051 A1* | 10/2007 | Hohl et al. | 604/891.1 |
| 2008/0009805 A1* | 1/2008 | Ethelfeld | 604/180 |
| 2008/0070599 A1 | 3/2008 | Apodaca et al. | |
| 2009/0157141 A1 | 6/2009 | Chiao et al. | |
| 2009/0157147 A1 | 6/2009 | Cauller et al. | |
| 2009/0240241 A1* | 9/2009 | Hyde et al. | 604/891.1 |
| 2011/0004076 A1* | 1/2011 | Janna et al. | 600/302 |
| 2011/0053546 A1* | 3/2011 | Hess et al. | 455/296 |

OTHER PUBLICATIONS

Inanlou, F.; Ghovanloo, M.; , "Wideband Near-Field Data Transmission Using Pulse Harmonic Modulation," *Circuits and Systems I: Regular Papers, IEEE Transactions on* , vol. PP, No. 99, pp. 1-1, Aug. 2010.

Kiani, M.; Ghovanloo, M.; , "A closed loop wireless power transmission system using a commercial RFID transceiver for biomedical applications," *Engineering in Medicine and Biology Society, 2009. EMBC 2009. Annual International Conference of the IEEE* , vol., no., pp. 3841-3844, Sep. 3-6, 2009.

Qingyun Ma; Haider, M.R.; Song Yuan; Islam, S.K.; , "Power-oscillator based high efficiency inductive power-link for transcutaneous power transmission," *Circuits and Systems (MWSCAS), 2010 53rd IEEE International Midwest Symposium on* , vol., no., pp. 537-540, Aug. 1-4, 2010.

Ghovanloo, M.; Najafi, K.; , "A wideband frequency-shift keying wireless link for inductively powered biomedical implants," *Circuits and Systems I: Regular Papers, IEEE Transactions on* , vol. 51, No. 12, pp. 2374-2383, Dec. 2004.

Haider, M. R.; Islam, S. K.; Mostafa, S.; Zhang, M.; Oh, T.; , "Low-Power Low-Voltage Current Read-Out Circuit for Inductively-Powered Implant System," *Antennas and Propagation, IEEE Transactions on* , vol. PP, No. 99, pp. 31-40, 0.

Hafliger, P.; Johannessen, E.; , "Analog to interval encoder with active use of gate leakage for an implanted blood-sugar sensor," *Biomedical Circuits and Systems Conference, 2008. BioCAS 2008. IEEE* , vol., no., pp. 169-172, Nov. 20-22, 2008.

Pengfei Li; Bashirullah, R.; , "A Wireless Power Interface for Rechargeable Battery Operated Medical Implants," *Circuits and Systems II: Express Briefs, IEEE Transactions on* , vol. 54, No. 10, pp. 912-916, Oct. 2007.

Asgarian, F.; Sodagar, A.M.; , "A high-data-rate low-power BPSK demodulator and clock recovery circuit for implantable biomedical devices," *Neural Engineering, 2009. NER '09. 4th International IEEE/EMBS Conference on* , vol., no., pp. 407-410, Apr. 29, 2009-May 2, 2009.

Colomer-Farrarons, J.; Miribel-Catala, P.; Rodriguez, I.; Samitier, J.; , "CMOS front-end architecture for In-Vivo biomedical implantable devices," *Industrial Electronics, 2009. IECON '09. 35th Annual Conference of IEEE* , vol., no., pp. 4401-4408, Nov. 3-5, 2009.

Selvakumaran, R.; Liu, W.; Soong, B.H.; Luo Ming; Loon, S.Y.; , "Design of inductive coil for wireless power transfer," *Advanced Intelligent Mechatronics, 2009. AIM 2009. IEEE/ASME International Conference on* , vol., no., pp. 584-589, Jul. 14-17, 2009.

Freudenthal, E.; Herrera, D.; Kautz, F.; Natividad, C.; Ogrey, A.; Sipla, J.; Sosa, A.; Betancourt, C.; Estevez, L.; , "Suitability of NFC for Medical Device Communication and Power Delivery," *Engineering in Medicine and Biology Workshop, 2007 IEEE Dallas* , vol., no., pp. 51-54, Nov. 11-12.

Haifeng Qian; Loizou, P.C.; Dorman, M.F.; , "A phone-assistive device based on Bluetooth technology for cochlear implant users," *Neural Systems and Rehabilitation Engineering, IEEE Transactions on* , vol. 11, No. 3, pp. 282-287, Sep. 2003.

Poon, A.S.Y.; O'Driscoll, S.; Meng, T.H.; , "Optimal Operating Frequency in Wireless Power Transmission for Implantable Devices," *Engineering in Medicine and Biology Society, 2007. EMBS 2007. 29th Annual International Conference of the IEEE* , vol., no., pp. 5673-5678, Aug. 22-26, 2007.

Marcus, A.; Davidzon, G.; Law, D.; Verma, N.; Fletcher, R.; Khan, A.; Sarmenta, L.; , "Using NFC-Enabled Mobile Phones for Public Health in Developing Countries," *Near Field Communication, 2009. NFC '09. First International Workshop on* , vol., no., pp. 30-35, Feb. 24-24, 2009.

* cited by examiner

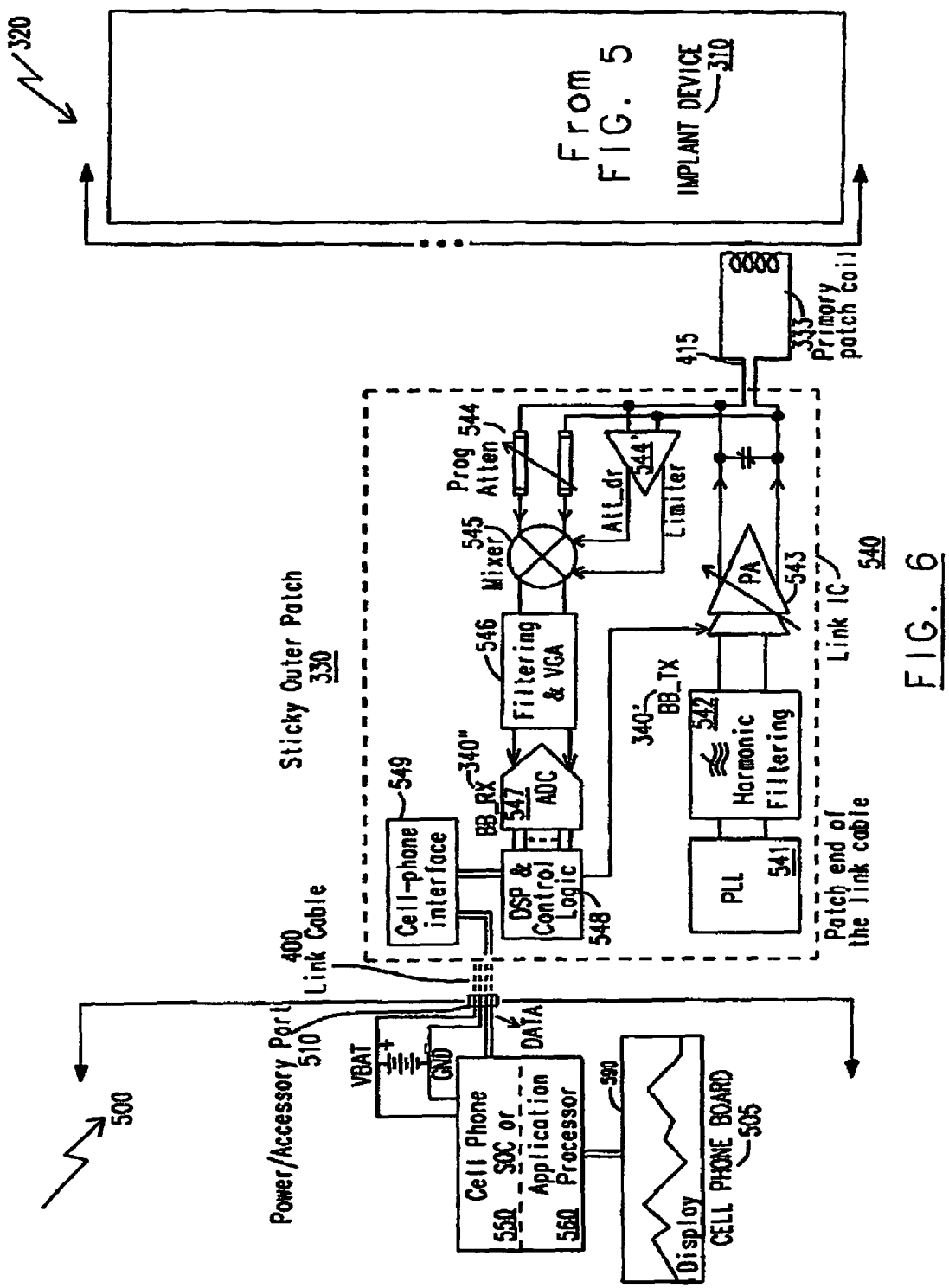

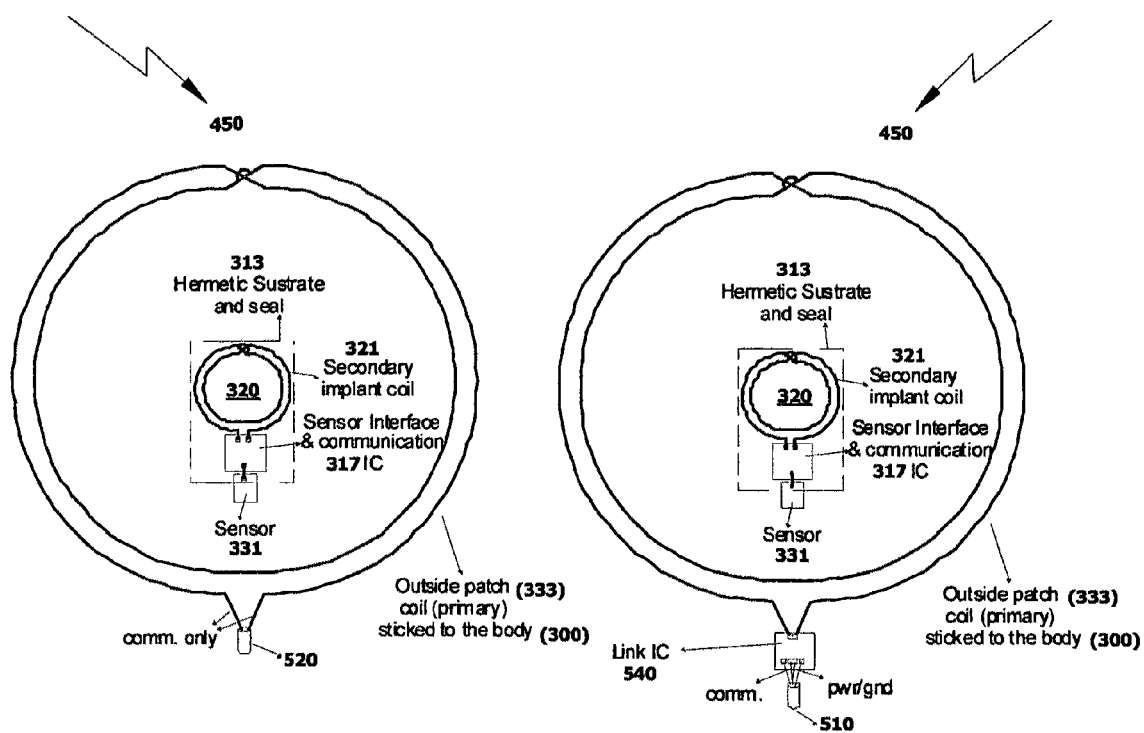
*FIG. 7a*      *FIG. 7b*

INTEGRATED MOBILE PHONE AND MEDICAL IMPLANT MONITORING SYSTEM AND METHOD FOR USING THE SAME

BACKGROUND

All references cited in this specification, and their references, are incorporated by reference herein where appropriate for teachings of additional or alternative details, features, and/or technical background.

Disclosed is a device configured to serve the function of a mobile-phone while at the same time being capable of communicating directly with a medical implant on the body of a person through an electronic umbilical cord.

Since the advent of the first cell phone (Motorola Dyna-Tac™) in 1973, the vision of its inventor, Martin Cohen, for "people to be able to carry their phones with them anywhere" has been realized several times over. Now, the ubiquitous cell phones (mobile-phones) are everywhere and are being used for multitude purposes. With the great mobility that these devices have provided and provide, they have assumed the function of serving as instant portals to weather, traffic advisories, and more importantly, to medical devices that wirelessly alert the cell phone owner of personal critical health conditions.

Publication US 2008/0070599 by Jennifer Apodaca, et al., describes a "Combined Cell Phone and Medical Monitoring Apparatus". The apparatus comprises a cellular phone or other wireless device combined with one or more medical monitoring devices, wherein the two devices share a single housing, power source, display, memory chip and data processor. The apparatus is capable of functioning as a separate medical apparatus and a normal cellular phone.

More specifically, according to Jennifer Apodaca, et al., the apparatus is directed to testing, monitoring diabetes indicators, and to storing, organizing, retrieving and transmitting test result and other medical data. The diabetes monitor of the invention measures blood sugar, though the invention is not limited to diabetes or the detection or monitoring of blood sugar.

Jennifer Apodaca, et al., show a block diagram of the apparatus 10 as illustrated in FIG. 1. The apparatus comprises a cell phone portion 15, blood sugar monitor portion 20 and a rigid housing (not shown). The cell phone portion 15 and the blood sugar monitoring portion 20 are secured within the housing. The cell phone portion 15 comprises a baseband portion 25, a radio module 30, a power amplifier module 35, a power management module 40, a rechargeable battery 45, a display 50, a keypad 55, an antenna 60, a filter diplexer 65 and a GPS receiver chip 70. The baseband module 15 comprises a baseband chip set, an audio module 75, and a radio to baseband interface 80, the audio module 75 comprising a microphone 90 and a speaker 95. The elements of the cell phone portion 15 are fixedly attached to the rigid housing.

Jennifer Apodaca, et al., describe the baseband chip set as comprising a data processing means and a data storage means. The data processing means is capable of processing data, extracting voice data from a microwave carrier, putting the outgoing voice on the carrier (modulation), controlling what data goes in and out of memory, taking in all commands, and/or outputting information to the display. The data processing means comprises a baseband processor and host controller 95. Keypad 55 allows the user/patient to interact with the data processing means. The central part of the baseband chip set portion 15, which is multi-functionally shared, provides the data storage means. The data storage means is operatively connected to the data processing means. The data storage means comprises random access memory ("RAM") and flash memory. The flash memory retains its contents when the unit is turned off and can be rewritten repeatedly. The memory 97 stores the startup procedure for the cell phone, last location from the GPS data, phone numbers, readings from the blood sugar monitor 20 with time tags, the owners medical history, and other critical or pertinent information. The baseband portion further comprises the radio to baseband interface 80 and the audio chip 75, which is operatively connected to a microphone 90 and a speaker 95. The GPS receiver chip 70 is operatively connected to the data processing means and the filter diplexer 65. The data processing means is operatively connected, directly or indirectly, to every component of the apparatus.

The blood sugar monitor portion 20 is also constructed as a chip set and an electro mechanical/chemical apparatus or an electronic apparatus, but functions separately from the cell phone portion of the apparatus, as taught by Jennifer Apodaca, et al. The blood sugar monitor portion 20 comprises a sample collector 23. The sample can be collected with a conventional finger prick and sample absorber, according to Jennifer Apodaca, et al. The blood or fluid sample is analyzed by light or electrical spectroscopy. The cell phone's baseband processor 95 is used to control this operation, calculate the test result and then place the output data in the cell phone's memory. The results of this test, along with recent history of the last few tests, are then sent to the cell phone's display 50 for the user/patient interface. Initiation of the test is signaled though the phone keypad 55 which has one or more additional keys dedicated to the blood glucose monitor or other medical apparatus in the preferred embodiment. This information is recorded in the unit's memory 97 along with a time tag. An accurate time tag is obtained from various sources, including the GPS and the cell tower.

The user/patient controls the functions of the cell phone 15 and the medical apparatus 20 through the cellular phone's keypad, which is operatively connected to the data processing means. The key pad is combined with a printed circuit board having terminals corresponding to the buttons. Keypad 55 of the apparatus 10 preferably comprises additional buttons (not shown) with functions related to the medical apparatus. The additional medical button specifically accesses medical information stored in the data storage of the phone. The button would bring up a menu on the display with categories of stored information, such as medical history, allergies, current medications, conditions and treatments and test results. One or more additional buttons, the monitoring buttons, turn on and control the medical apparatus 10, which comprises a blood sugar monitor. Alternatively, a standard keypad can be used to access a menu of functions to control the medical apparatus 10.

As Jennifer Apodaca, et al further describe, having performed all these functions, the baseband module 15 outputs an audio signal to the radio module 30 to modulate a carrier. That carrier is amplified in the power amplifier module 35 and sent to the antenna 60 for transmission. The antenna is connected to the system via filter diplexer 65. The purpose of the diplexer is to separate the received signals. One received signal is the cell phone signal which comprises incoming communications. The other signal is a GPS signal. The latter signal is processed in the GPS receiver chip 70 that calculates the position of the unit on the Earth. That information is then stored in the data storage means and frequently updated. The calculated result is then preferably transmitted along with the audio modulated carrier so that the cell phone company and any emergency responding authority can decode the signal and determine where the call is originating.

Thus, Publication US 2008/0070599 by Jennifer Apodaca, et al., describes a cell phone and a medical apparatus that are combined in a housing where both reside distinct from each other.

Still another art, U.S. Pat. No. 7,265,676 by Paul G. Gordon, et al., describes an "Alert System", and teaches " . . . A Method for An Implantable Medical Device" as shown in FIG. 2.

System 100 of FIG. 2, communicates between patient 110 and clinician 120. Alert system 100 includes implantable medical device ("IMD") 130 within patient 110, monitor 140, private network 150, patient management net-work 160, and patient management web clients 170/180 including patient browser 170 that is capable of displaying patient website 170a and clinician browser 180 that is capable of displaying clinician website 180a.

According to Paul G. Gordon, et al., system 100 shown in FIG. 2 is an alerting system for alerting a clinician 120 to an occurrence of an event detected by the implantable medical device 130 such as a pacemaker or defibrillator. The implantable medical device 130 includes a means for detecting the occurrence of the event and initiating a wireless transmission of data related to the event. The monitor 140 is configured to receive the wireless transmission of data and transfer the data. The patient management network 160 is configured to receive the data through private network 150 and store the data on a data storage device 163. The patient management network includes a web presentation service 190 for creating a website from the data stored on the data storage device, the website 170/180 configured to alert the clinician to the occurrence of the event. The patient management network 160 also includes device data input and interpretation module 161, web presentation services module 165, user/patient/web data storage 167, and core services module 169.

While the devices so described above are useful, what is needed is a system that integrates the available electronic resources that already exist in compact and portable devices, such as any generic mobile phone, with a body implantable medical device such that the sensory data obtained from the implant device can be transmitted directly to the mobile device where the data can be analyzed and presented in a user/patient-friendly manner to the patient/user/patient and/or transmitted wirelessly to a remote location for further action, if necessary, without the need for additional medical equipment.

REFERENCES

U.S. Pat. No. 6,083,248, "World Wide Patient Location and Data Telemetry System for Implantable Medical Devices". The system is for communicating with a medical device implanted in an ambulatory patient and for locating the patient in order to selectively monitor device function, alter device operating parameters and modes and provide emergency assistance to and communications with a patient. The implanted device includes a telemetry transceiver for communicating data and operating instructions between the implanted device and an external patient communications control device that is either worn by or located in proximity to the patient within the implanted device transceiving range. The control device preferably includes a communication link with a remote medical support network, a global positioning satellite receiver for receiving positioning data identifying the global position of the control device, and a patient activated link for permitting patient initiated personal communication with the medical support network. A system controller in the control device controls data and voice communications for selectively transmitting patient initiated personal communications and global positioning data to the medical support network, for initiating telemetry out of data and operating commands from the implanted device and transmission of the same to the medical support network, and for receiving and initiating re-programming of the implanted device operating modes and parameters in response to instructions received from the medical support network. The communications link between the medical support network and the patient communications control device may comprise a world wide satellite network, hard-wired telephone network, a cellular telephone network or other personal communications system. Methods and apparatae are also described that enhance the ability of the medical system to find patients and to get reports on patient and medical device status, and even update medical device programming using such facilities, and others described in detail within.

U.S. Pat. No. 7,787,946, "Patient Monitoring, diagnosis, and/or Therapy systems and Methods." Systems and methods involve an implantable device configured to perform at least one cardiac-related function, a patient-external respiratory therapy device, and a communication channel configured to facilitate communication between the implantable device and the respiratory therapy device. The implantable and respiratory therapy devices operate cooperatively via the communication channel to provide one or more of patient monitoring, diagnosis, and therapy. The communication channel is configured to facilitate communication between an external processing system and at least one of the implantable device and the respiratory therapy device. The processing system is communicatively coupled to at least one of the implantable and respiratory therapy devices via the communication channel to provide one or more of patient monitoring, diagnosis, and therapy.

U.S. Pat. No. 7,181,505 describes a method and corresponding system for updating or installing new software loaded into the memory of an implantable medical device (IMD) implanted within a body of a patient is described.

U.S. Pat. No. 7,613,510 shows a "Biofeedback Device Displaying Results on a Cellular Phone Display." Biofeedback information is measured at a body part of a user/patient. The information is communicated to a cellular telephone device and used to produce a display on a display screen of the cellular telephone device.

U.S. Pat. No. 7,324,850 discloses systems and methods for telemetric communication between a handheld programmer device and an implantable medical device. The hand-held comprises a touch-sensitive screen that allows the user/patient to visually observe and control the handheld's operation. The hand-held further comprises an internal and/or external analytical means to provide analytical capabilities which can also be configured as a component of an Advanced Patient Management System.

U.S. Pat. No. 7,400,257 teaches integration of medical monitoring technologies with wireless networks to wirelessly send signals from a monitoring device to a cellular telephone or other personal electronic device (PED). A sensor is placed inside or on the patient's body. Information from the monitoring sensor is transmitted to a nearby and/or remote PED. The information transmitted to the PED is then displayed, processed, stored or forwarded to another location if needed. The monitoring system monitors a variety of bodily processes, but preferably measures vital signals such as heart rate, blood pressure, respiration rates, etc. The disclosed system can also be used to monitor glucose levels in diabetic user/patients as well as an alert system to alert the patient and third parties when a patient experiences an adverse medical condition.

U.S. Pat. No. 7,181,505 teaches a method and corresponding system for updating or installing new software loaded into the memory of an implantable medical device (IMD) implanted within a body of a patient.

U.S. Pat. No. 7,613,510 shows biofeedback information measured at a body part of a user/patient. The medical device used communicates the medical information to a cellular telephone device where the information is displayed on a display screen of the cellular telephone device.

U.S. Pat. No. 7,324,850 teaches systems and methods for telemetric communication between a handheld programmer device and an implantable medical device. The medical device comprises a user/patient-friendly, color, touch-sensitive screen that allows the user/patient to visually observe and control the handheld operation.

U.S. Pat. No. 7,156,809 describes method and apparatus for health and disease management combining patient data monitoring with wireless Internet connectivity.

U.S. Pat. No. 7,722,536, describes a glucose measuring device integrated into a holster for a personal area network device.

U.S. Pat. No. 7,400,257, teaches medical monitoring technologies integrated with wireless networks to wirelessly send signals from a monitoring device to a cellular telephone or other personal electronic device (PED).

U.S. Pat. No. 7,395,117 shows a medical device capable of utilizing a pervasive wireless communications network, such as a digital wireless telephone network, personal communication services network or pager network, to directly communicate with a host computer without the need for a repeater device.

SUMMARY

Aspects disclosed herein include
an integrated mobile device and medical implant system comprising a first architecture further comprising; a mobile electronic device integrated with an implantable device in body of a user/patient through an electronic umbilical cord having an implant-end implanted with the implementable device, and a phone-end attachable to the mobile electronic device; the implantable device comprising an implant coil and an implant IC hermetically sealed within a substrate; the electronic umbilical cord providing inductive communications link between the implantable device and the mobile electronic device through a patch coil affixed to the implant-end patch; the implant-end patch further comprising an outer portion configured to receive a Link-ICC acting as an interface between the electronic device and the implantable device through the electronic umbilical cord; the umbilical cord further comprising a two-way near field inductive data/power transfer two-wire cable capable of carrying modulated RF data; a Link-ICC formed in the mobile phone between a communication port and system-on-chip chip (SOCC), or inside the SOCC, or inside application processor (AP), and capable of acting as an interface between the mobile electronic device and the implantable device through the electronic umbilical cord; wherein the Link-ICC is programmable to work in an RF-ID band to generate a carrier signal for fully differential operation for interference-free communication with the implantable device through the electronic umbilical cord, and further configured to have a power amplifier that drives the primary patch coil at the phone-end of the electronic umbilical cord, and a receive chain including a programmable attenuator, a limiting amplifier to recreate a carrier signal for mixing, filters and variable gain amplifiers (VGAs) for signal conditioning, and ADC for conversion to digital signal, a digital signal processor and control logic to extract data from the implantable device, a mobile electronic device interface to present the data to mobile electronic device application processor; a mobile electronic device display to present processed data to immediate user/patient and/or an antenna to communicate data wirelessly to a remote location; and wherein, the electronic mobile device is capable of functioning both as a normal mobile phone, as a medical monitoring device, or both simultaneously, without any interference between two modes of operations, with switch of software application from a drop-down menu inside the mobile phone, an integrated mobile device and medical implant system comprising a second architecture further comprising; a generic mobile phone; the generic mobile phone integrated with an implantable device through an electronic umbilical cord having an implant-end implanted with the implementable device, and a phone-end attachable to the mobile phone; the electronic umbilical cord having an implant-end patch and a phone-end plug, the electronic umbilical cord comprising standard power/accessory cable including digital interface wires and power supply wires; the implant-end patch further comprising an outer portion configured to receive a Link-ICC acting as an interface between the mobile phone and the implantable device through the electronic umbilical cord; wherein the Link-ICC is programmable to work in an RF-ID band to generate a carrier signal for fully differential operation for interference-free communication while connected to the mobile phone through the electronic umbilical cord, and further configured to have a receive chain including a programmable attenuator, a limiting amplifier to recreate a carrier signal for mixing, filters and variable gain amplifiers (VGAs) for signal conditioning, and ADC for conversion to digital signal, a digital signal processor and control logic to extract data from the implantable device, a mobile phone interface to present the data to mobile phone application processor; a generic mobile phone display to present processed data to immediate user/patient and/or an antenna to communicate data wirelessly to a remote location and wherein, the electronic mobile device is capable of functioning both as a normal mobile phone, as a medical monitoring device, or both simultaneously, without any interference between two modes of operations, with switch of software application from a drop-down menu inside the mobile phone, a method comprising providing a first architecture having a mobile phone configured to receive an interface Link-ICC and an implantable device communicating through the interface Link-ICC via an electronic umbilical cord having an implant-end patch and a phone-end plug, the implantable device comprising an inductive implant coil, implant IC and biosensors sealed within a substrate; placing a patch coil on the implant-end patch of the electronic umbilical cord; placing the Link-ICC inside the mobile phone between a communication port and system-on-chip chip (SOCC), or inside the SOCC, or inside application processor (AP); securing adhesively the implant-end patch of the electronic umbilical cord onto body of the user/patient over the implantable medical device; connecting the phone-end of the electronic umbilical cord further comprising a two-way near field inductive data/power transfer two-wire cable capable of carrying modulated RF data to the mobile phone; turning on the mobile phone; having a battery; clicking on drop-down menu of the mobile phone to choose between multiple of modes operation; the modes of operation comprising at least functioning as a mobile phone and a medical monitoring device simultaneously, or as a stand-alone medical monitoring device, or as a standard mobile phone; transceiving data to and from the implantable medical device; and presenting processed data in a useful format to user/patient and/or transmit wirelessly to a remote location, a method comprising providing a second architecture having a generic mobile phone and an implantable medical device communicating through an interface Link-IC via an electronic umbilical cord having an implant-end patch and a phone-end plug, the implant-end patch having an outer portion, the implantable medical device comprising an inductive implant coil, implant IC and biosensors sealed within a substrate; placing an inductive patch coil on the implant-end patch of the electronic umbilical cord; placing the Link-ICC on the outer portion of the implant-end patch of the electronic umbilical cord; enabling the Link-ICC to affect power/data transfer with the implantable device through the inductive patch coil and inductive implant coil; securing adhesively the implant-end patch of the electronic umbilical cord onto body of the user/patient over the implantable medical device; connecting the phone-end of the electronic umbilical cord further comprising standard power accessory cable which contains standard digital data communication wires and power supply lines; turning on the mobile phone having a battery; clicking on drop-down menu of the mobile phone to choose between multiple of modes operation; the modes of operation comprising at least functioning as a mobile phone and a medical monitoring device simultaneously, or as a stand-alone medical monitoring device, or as a standard mobile phone; transceiving data to and from the implantable medical device; and presenting processed data in a useful format to user/patient and/or transmit wirelessly to a remote location.

BRIEF DESCRIPTION OF DRAWINGS

FIG. 6 shows the placement of a Link-ICC on the implant-end of an electronic umbilical EU-cord according to the present disclosure.

FIG. 7a shows the cable connection of the phone-end of the EU-cord to any available port on a mobile phone configured to receive a Link-ICC, according to the first architecture of the present disclosure.

FIG. 7b shows the cable connection of the phone-end of the EU-cord to the power/accessory port of a generic mobile phone which supplies power to a Link-ICC that is placed on a patch at the implant-end of EU-cord, according to the second architecture of the present disclosure,

DETAILED DESCRIPTION

Figure 1:
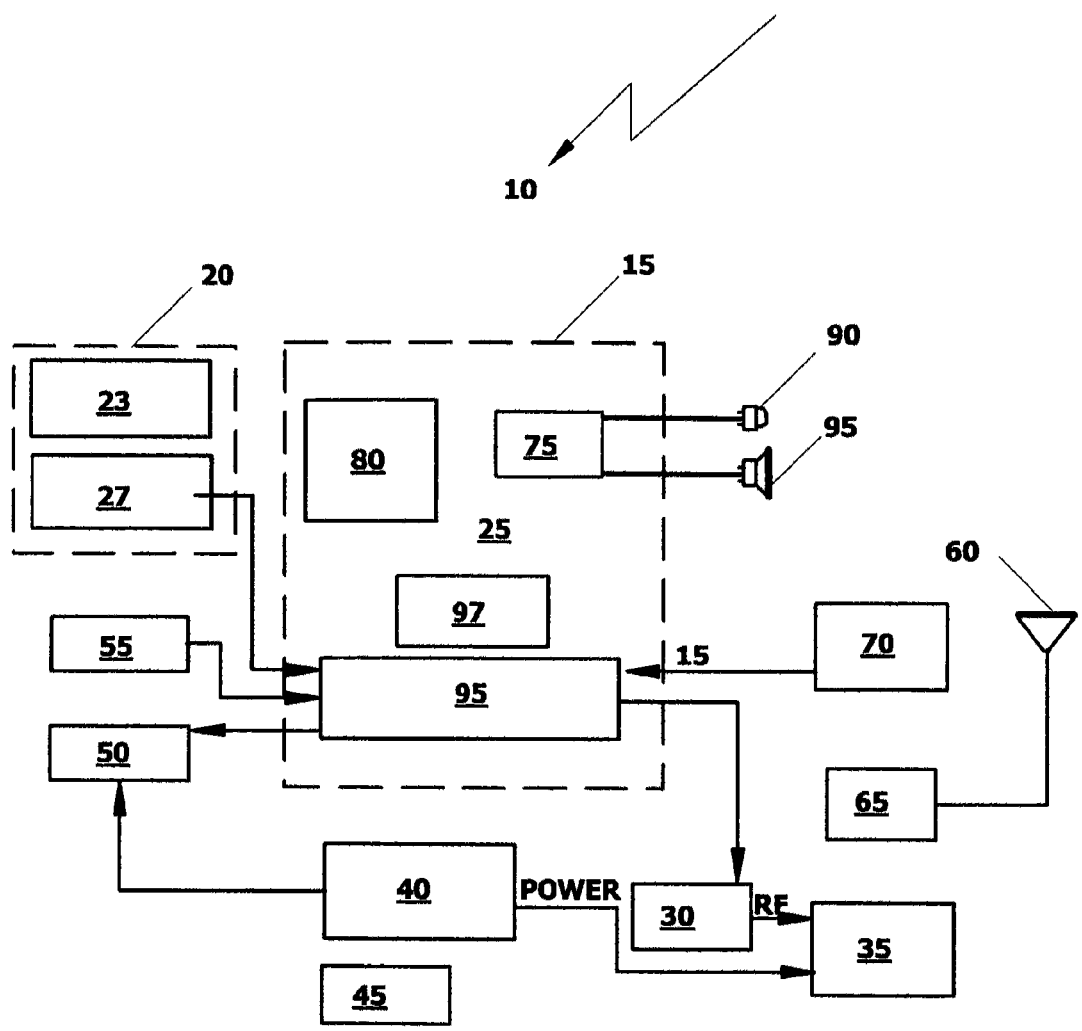
FIG. 1 shows a cell phone and a medical monitoring apparatus combined in a housing, according to prior art.
Figure 2:
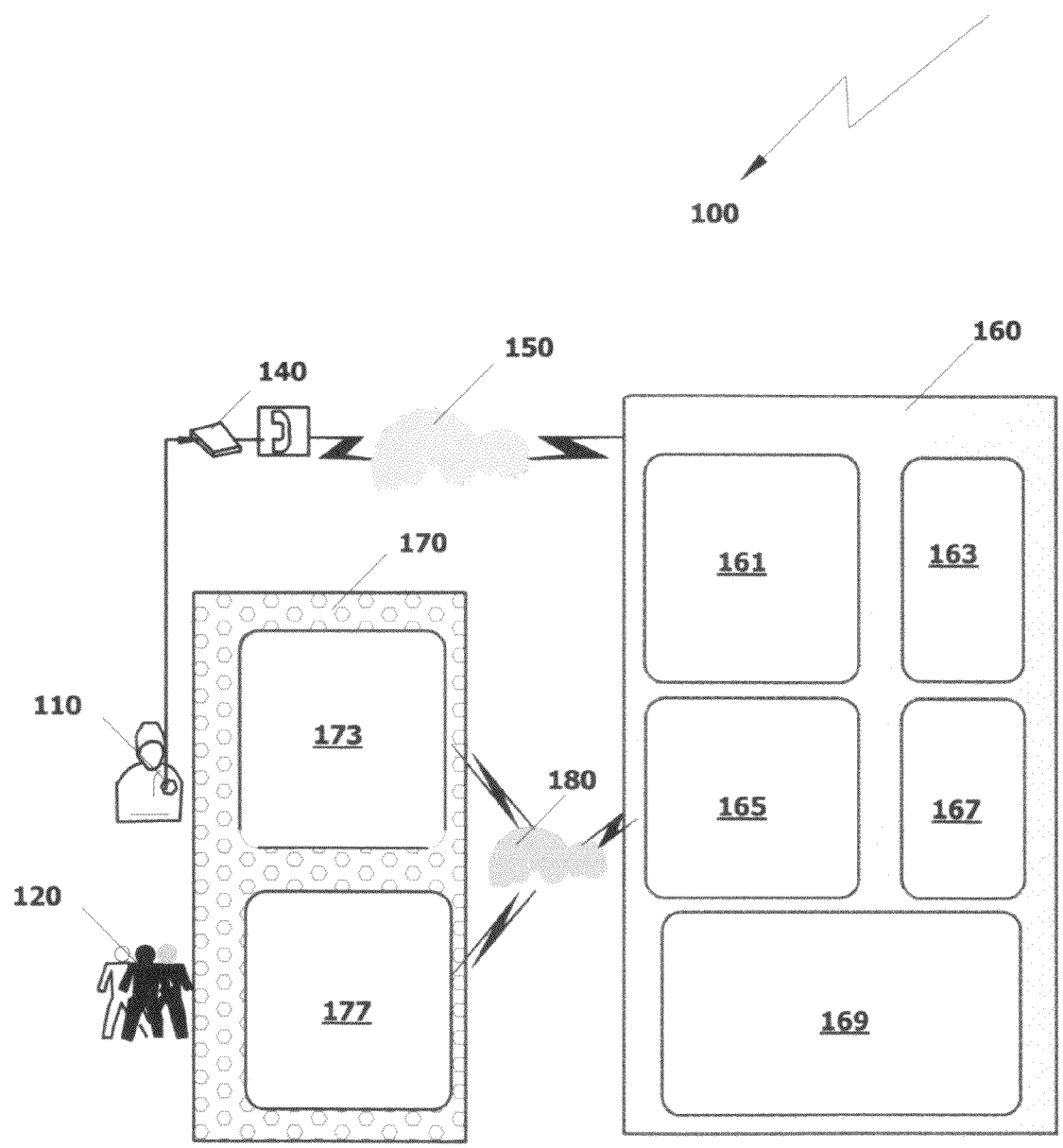
FIG. 2 shows an alert system, according to prior art.

In embodiments there is illustrated:

an integrated mobile phone and medical implant system, and method of integrating the system. The disclosed system integrates the available electronic resources that already exist in compact and portable devices, such as a mobile phone, with a body implantable medical device such that the sensory data obtained from the implant device can be transmitted through an electronic umbilical cord directly to the mobile device where the data can be analyzed and presented in a user/patient-friendly manner to the user/patient and/or transmitted wirelessly to a remote location for further action, if necessary, without the need for additional medical equipment; and in particular, a cell phone based integrated medical implant system is disclosed. It will be evident to those skilled in the art that, unlike in prior art, no additional external interface device other than the cell phone is required. As described in detail below, a Link-ICC (integrated circuit chip) is incorporated into the cell phone electronics to manage communications between the medical implant and the cell phone while preventing any interference with the system-on-chip chip (SOCC) which manages the normal cell phone functions. The Link-ICC may also be integrated into SOCC. In either case, Link-ICC enables simultaneous reception in the cellular and other wireless communication bands without any interference. This is accomplished by not using cell phone communication bands, but rather using standard RF-ID bands to communicate with the implant device through a wired link. The same link, which serves the function of an "umbilical cord," between the user/patient/patient and the cell phone, is used to transfer power as well to the implant device, as described below. Hence, the disclosed system comprises three parts, namely, the implantable device, the umbilical cord link having a user/patient/patient passive coil patch at the implant end, and the cell phone, to which the phone-end of the umbilical cord is attached. By incorporating an additional user/patient software interface, any of the data/power/accessory ports, such as audio jack, micro-USB port or the regular communication/programming ports can be allocated for implant communication without sacrificing any regular cellphone communication functionality. The disclosed system, therefore, provides to the user/patient/patient a capability for monitoring the implant device as well as cellular communication simultaneously.

The disclosed system further employs all the available mobile phone resources such as display, battery, communication and accessory ports, application processor, crystal oscillator, audio, vibrator, memory etc., to form a complete medical monitoring interface to the user/patient without the need for any additional medical devices. The system prevents any unwanted conflicts or interferences with regular cell phone communications. This is accomplished by providing a direct inductive wired communication link, or an electronic umbilical EU-cord, between the implantable device and the mobile device to transfer power to the implant device as well as to transmit sensory data to the mobile device via RF-ID bands; and, a link integrated circuit chip, or, Link-ICC, that manages and coordinates the communications between the mobile device and the implant device. The EU-cord has an implant-end which is adhesively adhered proximate to the implantable medical device in the body of the patient/user/patient, and a phone-end which connects to the phone accessory/communication ports. The communication with the implant and the mobile device is provided though software interface which is allocated through any of the data/power/accessory ports, such as audio jack, micro-USB port or the regular communication/programming ports without loosing any regular cell phone functionality. With this wired technique, the use of a large standard communication cellular or other wireless chip sets (GSM, Bluetooth, WLAN, etc.) in the implant device is avoided, thus relieving the user/patient of discomfort. Hence, two architectures are disclosed; a first architecture where the Link-ICC resides inside the mobile phone, and a second architecture where the Link-ICC resides on a patch adjacent to the implantable device as described further in the following paragraphs and drawings. It will be evident that with the second architecture no modifications will be required to be made to the mobile phone.

Figure 3:
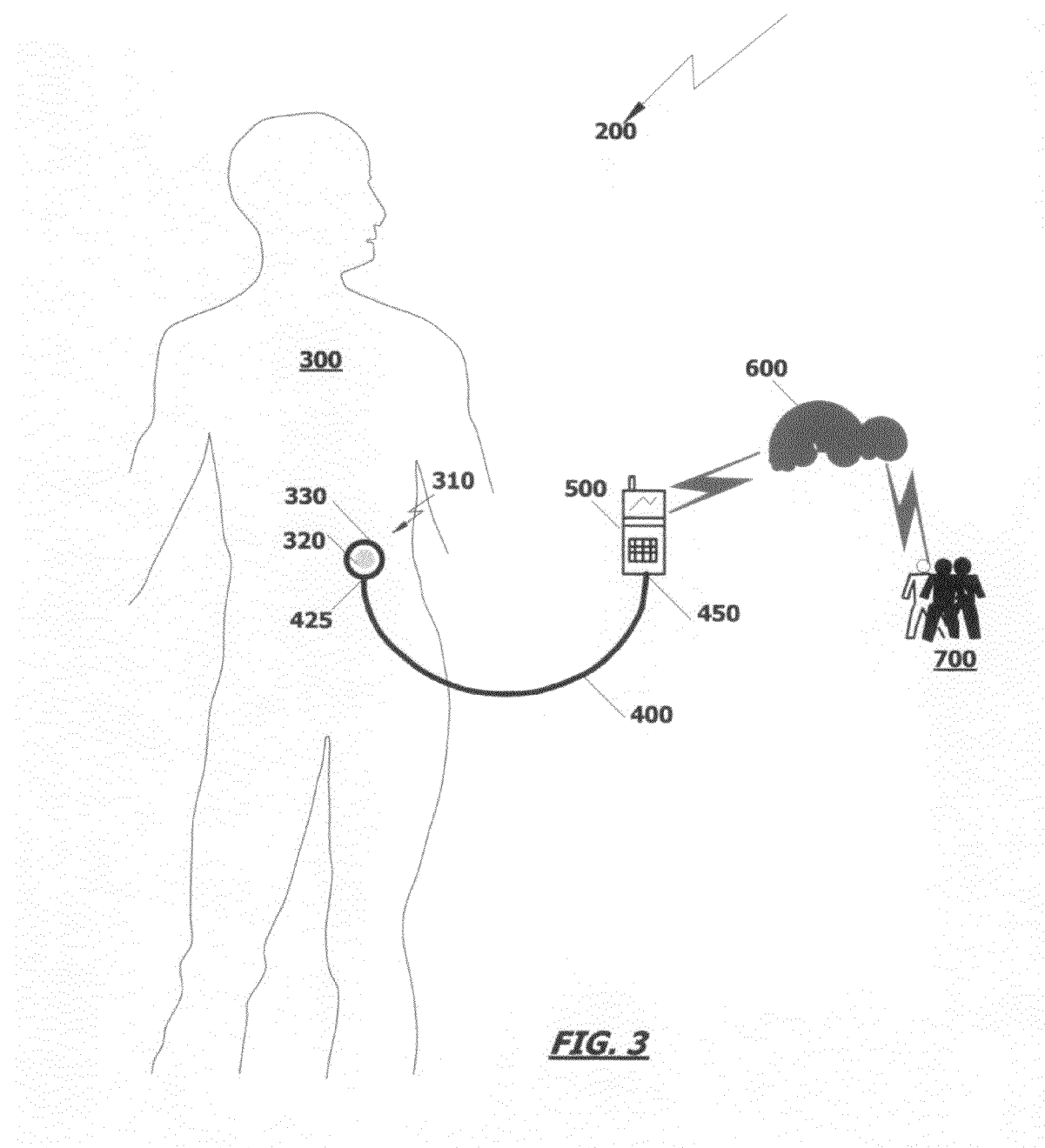
FIG. 3 shows an integrated mobile phone and medical implant monitoring system according to the present disclosure.

Now referring to the drawings, FIG. 3 discloses a system 200 that provides communications not only directly and reliably with an implantable device 310 through an electronic umbilical (EU)-cord 400, but also wirelessly to the universe 600 in an interference free manner between voice and data signals in a more compact and portable device 500 that can be taken anywhere along with the implantable device 310 while providing integrated data storage and data analyses, graphical presentation, and critical alerts 510 to the user/patient 300 as well as to a clinic 700, from which the necessary help may be provided to the implant wearer 300 via the portable device 500 as needed. System 200 comprising the primary components, namely the implantable device 310, the EU-cord 400 and the mobile device 500 provides a self-contained, light and portable system which shares all the available mobile device (usually called cell phone in the US) resources such as display, battery, communication and accessory ports, application processor, crystal oscillator, audio, vibratory element, memory and other features that are well-known to those involved with the art, to form a complete medical monitoring interface to user/patient user/patient/patient 300. The instant disclosure provides a wired communication link through the EU-cord 400 to obviate interference between wired communication with the implantable device 310 and the wireless communication with the outside universe 600. All components that are necessary for system 200 to function both as a mobile device as well as a medical device separately, as well as in cooperation with each other are shared between the implantable device 310, the (EU) Cord 400 and wireless mobile device 500 independent of any other device. The EU-cord 400 that is connected to outside patch coil 333 of the implant device 310—as further explained in the paragraphs and illustrations that follow—forms the near-field inductive data/power link between the integrated mobile device 500 and the implant device More specifically, implantable device 310 comprises implantable components including bio-sensors 331, actuators 337, signal conditioning and communication implant coil 321, as better seen in FIGS. 5 and 6. Disclosed also is an outside data/power coil, which is placed on the outer periphery or portion of the sticky patch 330 at the implant-end 425 of the EU-cord 400, as will be explained further below in FIGS. 5, 6 and in FIGS. 7a and 7b.

Cable 400, shown in FIG. 3 serves the function of an "electronic umbilical cord," or EU-cord, for it provides a life line for transmitting vital information from implant 310 to a mobile device 500 through a port 510. EU-cord is a near-field inductive data/power cable link, as will be described later. Port 510 can be an audio jack, a micro-USB accessory interface or any power/accessory interface port, as further explained in FIG. 6.

Figure 4:
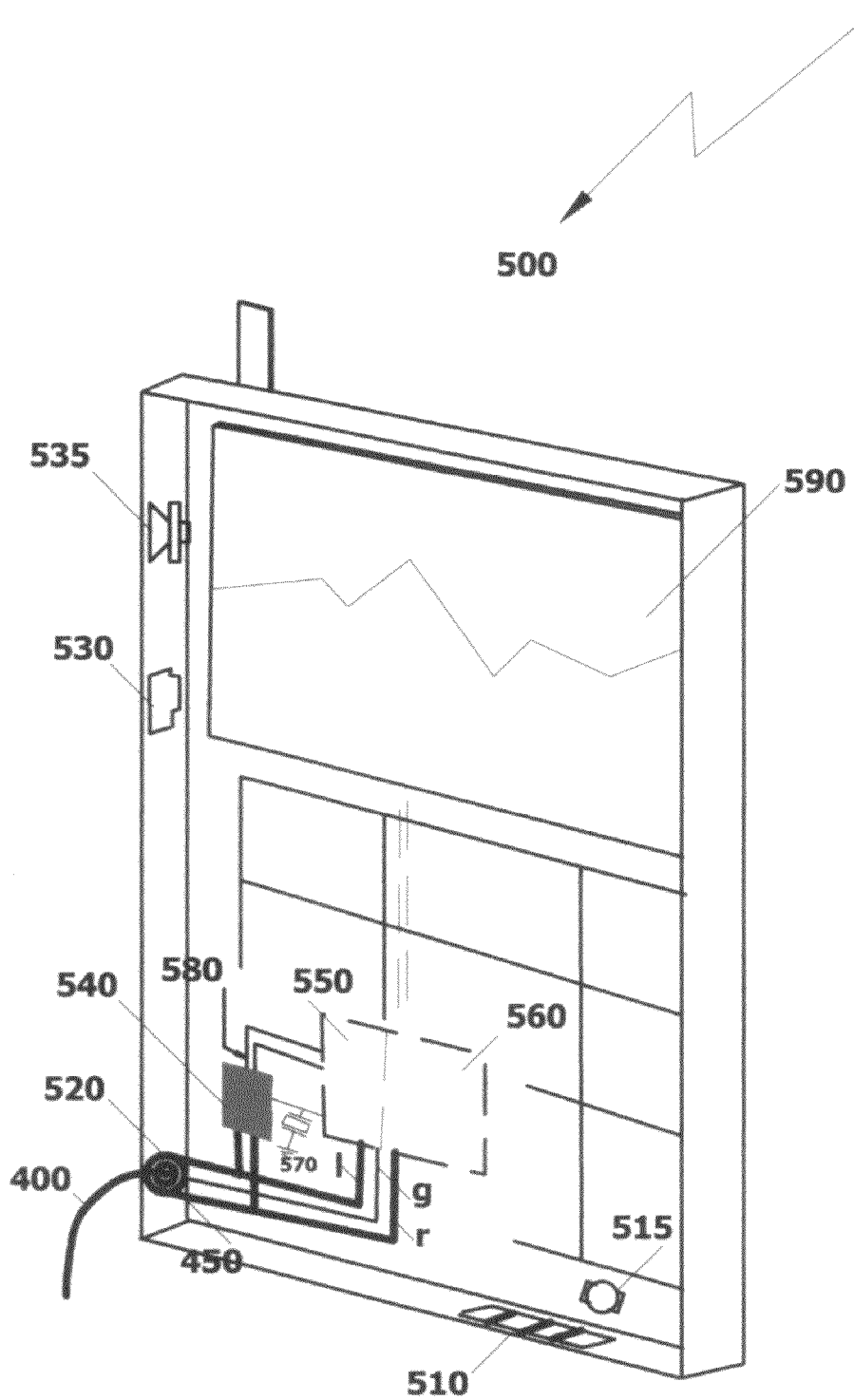
FIG. 4 shows an embodiment of a mobile phone configured to receive a Link-ICC according to the present disclosure.

A schematic representation of a mobile device 500 is shown in FIG. 4. Power/accessory port 510, vibrato 515, audio accessory jack 520, micro-USB port 530 and speaker 535 are also shown in the same FIG. 4. In one aspect of the present disclosure, a Link-ICC 540 is provided within the mobile device 500 to serve the function of an interface between the mobile device 500 and the implantable device 310 through the electronic EU-cord 400. Integration of the Link-ICC 540 inside the mobile device 500, as the first architecture of the present disclosure, enables the user/patient not to carry additional device with a battery, display, Light-Emitting-Diode (LED) and other accessories, which otherwise would be required. In another aspect, the same Link-ICC 540 can be integrated into the mobile SOCC 550 or into application processor (AP)-IC 560 of the mobile phone 500 shown in the same FIG. 4. By integrating the Link-ICC into either the SOCC 550 or the (AP)-IC 560, the footprint of the mobile device 500 is reduced, while at the same time reducing the cost. Link-ICC 540 in FIG. 4 is shown to use audio jack 520 for the implant 310 communication purposes through EU-cord 400, but it will be understood that Link-ICC 540 can also use any of the other ports shown in FIG. 4, such as the data/power/accessory port 510, the micro-USB port 530 or any other communications/programming ports available in a mobile phone, or any generic mobile phone, as described in a second architecture of the presently disclosed system. It will be noted in FIG. 4 that the fully differential Link-ICC 540 outputs share the left-right (l-r) audio headset drive lines (which could also be made single-ended, as it will be understood by those skilled in the art). It will also be understood that having a matching audio connector at the cell-phone end 520 of the connecting EU-cord 400 allows reuse of the port for the medical monitoring purposes without any modification in the cell-phone interface. The user/patient can switch headset audio jack functionality to the medical monitor mode through the software in mobile phone 500 to avoid any conflict in driving port 520. In one aspect of the present disclosure, a software drop-down menu is provided in the cell-phone in which the user/patient can choose the implant monitoring mode, whereby the cell phone processor disables the headset driver which is used for music and other multimedia applications and releases the port for medical communication purposes. The fully differential signaling through EU-cord 400 mitigates any undesired interference to the cellular or other wireless bands. It will be understood by those skilled in the art that differential signaling, through EU-cord affects implant device communication immune to any type of unwanted interferences as well.

As still another aspect, it will be evident to those skilled in the art that while the various electronic components shown in FIG. 4 such as battery 570, reference crystal oscillator 580, ports 510, 520, 530 and display 590 of the mobile device 500 are used and shared for Link-ICC 540, several other cell-phone electronic components, such as application processor (AP)-IC 560, memory, audio speaker 535 and vibrator 515, such as shown in FIG. 4 can be utilized for additional side functions relating to the implant system. In the specific case of continuous glucose monitoring system for example, display 590 can be used to plot the continuous graph of the glucose level of the patient with a desired measurement sample frequency throughout the day. If desired, the cell-phone memory can be used to store the glucose level measurements to present a long term statistical data to the user/patient. If any preset limits were observed, the user/patient can be warned through speaker 535 and even with the vibrator 515. In case of an extreme condition that may put the patient into an unconscious state (extremely low glucose levels), the mobile phone 500 can call the predefined number of care provider or relative playing a prerecorded message corresponding to that particular emergency condition.

Figure 5:
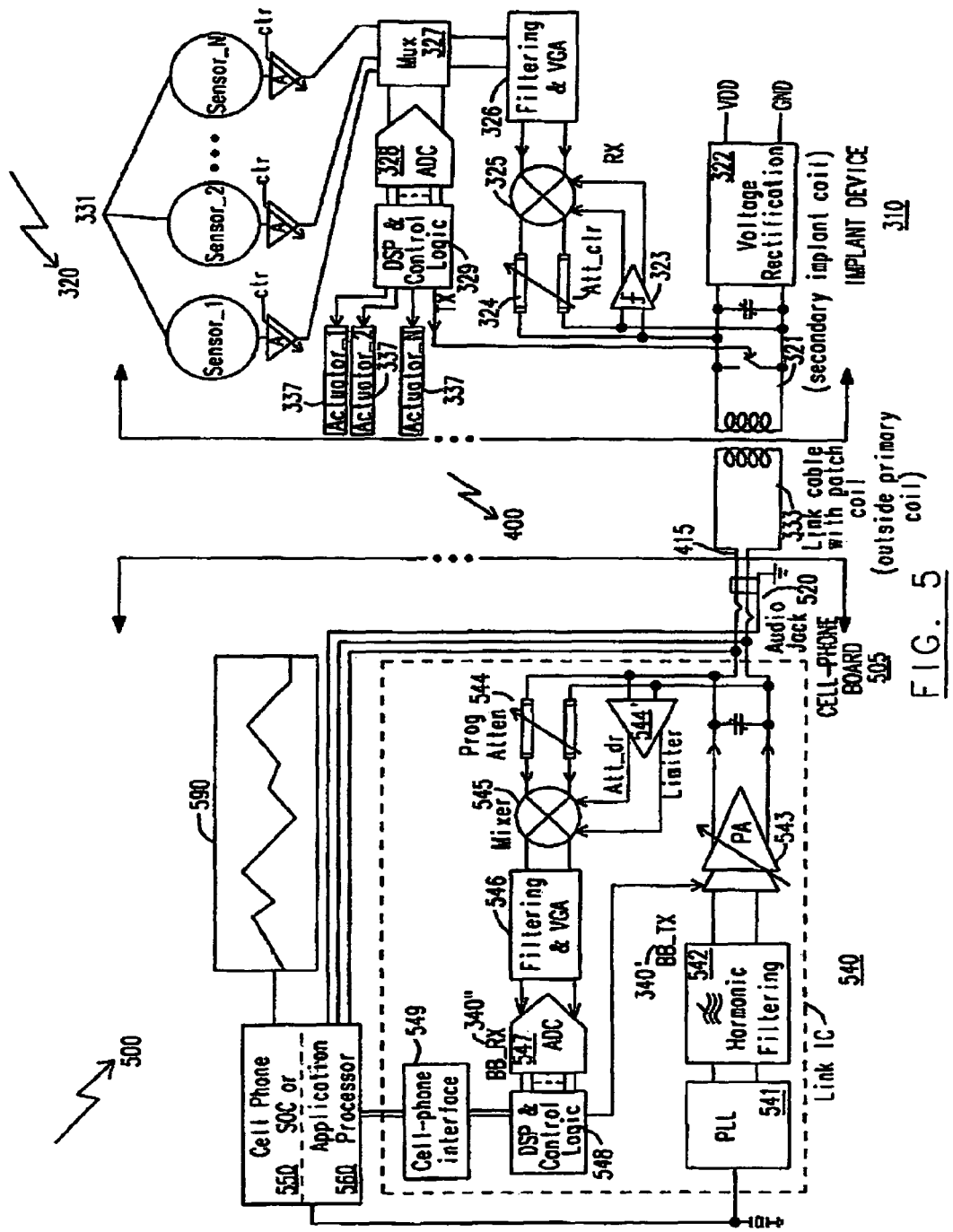
FIG. 5 shows the placement of a Link-ICC in a mobile phone of the integrated system of the present disclosure.

In the first architecture of the disclosure as described above, where Link-ICC 540 is placed on the mobile device 500, the various components that are utilized in the mobile device 500 versus the components that are used in the inner portion 320 of the implant device 310 are better shown in FIG. 5. In the second architecture of the present disclosure as described below, where Link-ICC 540 is placed in the outer sticky patch portion 330 of the implant device 310 is better shown in FIG. 6. It will be noted that in both architectural aspects, components in Link-ICC 540 and components in the inner portion 320 remain the same except for the placement of Link-ICC 540, that is, whether on the mobile phone board 505 of the mobile device 500 or in the outer patch 330 of the implantable device 310.

Link-ICC 540 shown in FIGS. 5 and 6 comprises well-known components, including fractional Phase Lock Loop, PLL 541, Harmonic Filter 542, Power Amplifier, PA 543, Programmable Attenuator 544, Mixer 545, Filtering and variable gain amplifiers VGA 546, ADC 547 for signal conversion to digital, DSP 548 for digital signal processing and mobile phone interface 549.

FIGS. 5 and 6 also show implantable device inner portion 320 comprising well-known components, including coil 321, voltage rectifier 322, limiter 323, attenuation controller 324, mixer 325, Filter&VGA 326, Mixer 327, digital converter ADC 328, digital signal processor (DSP) 329 and several medical sensors and actuators 331.

In yet another aspect of the present disclosure, the placement of Link-ICC 540, when inside the mobile device 500, as shown in FIG. 5, or on the sticky outer patch 330, as shown in FIG. 6, alters the implant end 330 of the integrated mobile phone and medical implant system 200 as shown in FIGS. 7a and 7b.

FIG. 7a shows the cable connection of the phone-end 450 of the EU-cord 400 to any available port, such as ports 510, 520 or 530 on a mobile phone 500 shown in FIG. 4 configured to receive Link-ICC 540, according to the first architecture of the disclosed integrate system 200.

FIG. 7b shows the cable connection of the phone-end 450 of the EU-cord 400 to the power/accessory port 510 (FIG. 4) of a generic mobile phone 500 which supplies power to Link-ICC 540 that is placed on a patch 333 at the implant-end 425 of EU-cord, 400 according to the second architecture of the presently disclosed system.

It will be noted that the inner portion 320 of the medical implant 310—comprising a hermetic substrate and seal 313, an implant coil 321, a sensor interface and communication IC 317, sensors 331, including actuators 33—is common to both implant ends 425 shown in FIGS. 7a and 7b is corresponding to the first and second architectures, respectively. However, the implant-end 425 of the EU-cord will differ whether the outer patch 333 is with or without Link-ICC 540 and EU-cord 400 will also differ accordingly for it would need to have additional power supply lines as well to feed the Link-ICC 540 from the mobile phone 500, as described below. It will be understood, however, that the two types of EU-cords may be combined to one link cable having a universal phone-end to plug into any available port on any mobile phone.

In an aspect of the first architecture shown in FIG. 5, where Link-ICC 540 is placed inside mobile device 500, the EU-cord 400 connects to audio jack 520 as shown in the same FIG. 5 and also schematically in FIG. 7a. In this case, the electronic umbilical EU-cord further comprises a two-way near field inductive data/power transfer two-wire cable capable of carrying modulated radio frequency (RF) data. The two wires 415 in the EU-cord 400 terminate at the primary patch coil 333 as shown in FIG. 5. Wires 415 carry RF signal which is used for both data communication and power transfer. Since Link-ICC is inside the mobile phone and can access the power therein, no power line is required in the case of the first architecture disclosed in FIG. 5

In another aspect corresponding to the second architecture shown in FIG. 6, where Link-ICC 540 is placed on the sticky outside patch 330, EU-cord 400 connects to power/access port 510 as shown in the same FIG. 6 and also schematically in FIG. 7b. It will be understood that by moving the Link-ICC to the outer patch 330 of the second architecture system shown in FIG. 6, any generic mobile device having the characteristics of a cell phone may be used, without any modifications, as a part of the integrated mobile phone and medical implant monitoring system of the present disclosure. In the second architectural system shown in FIG. 6, the umbilical EU-cord 400 comprises two-way near field inductive data/power transfer cable containing standard power accessory cable and standard digital data communication wires and power supply lines. It will be noted that in the second architecture case shown in FIG. 7b, the connection is made to power/access port 510, because access to DC battery supply is needed for Link-ICC 540 that resides on the outer patch 330. By the same token, in the first architecture case shown in FIG. 7a, the connection is made to audio jack 520, because Link-ICC 540 already resides in the mobile device 500 and has access to power internally to share. However, the connection for the latter case shown in FIG. 7a can be made to power/access port 510 if port 510 is not available. In both cases shown in FIGS. 7a and 7b, reference numeral 333 denotes the coil on the sticky outside patch that gets adhered to user/patient's body 300 shown in FIG. 3. The EU-cord 400 that is connected to 333 forms the near-field inductive data/power link between the integrated mobile device 500 and the implant device 310. The outside patch coil 333 number of turns as well as the implant coil 321 number of turns can be optimized to deliver maximum power and reliable data. This patch coil 333 can be arranged to stick to the body proximate to implant device 310 with minimal disturbance to the user/patient. (See FIGS. 3 and 7a&7b). The disclosed wired technology enables the use of much smaller implant coil compared to wireless implant technologies and hence does not pose a substantial disturbance for the patient carrying the implant. In FIGS. 7a and 7b, the implant IC 317, coil 321, and the sensors 331 are connected to ease the final hermetic packaging 313 of the implant 310. If desired, the implant coil 321 can be integrated into the implant IC 317 reducing the area and cost further with some loss in communication link sensitivity performance.

The dot-dash lines in the wiring diagrams of the first and second architectures shown in FIGS. 5 and 6, respectively, delineate schematically the boundaries between the mobile device 500, outside connecting patch cable with coil associated with the EU-cord 400 and the implantable device 310. As it will have been evident from the descriptions above, the Link-ICC 540 provides the function of a communication IC and is employed as an interface between the implant device 310 and mobile device electronics shown in FIGS. 5 and 6. As an embodiment of the present disclosure, Link-ICC 540 can readily share all the resources available in the mobile device 500 such as power supplies 570, reference crystal oscillator 580, physical board substrate etc. that are needed for its operation. Moreover, using the same crystal frequency reference the implant link through EU-cord 400 can be fully synchronous with the mobile phone and other wireless bands and hence a careful frequency planning can guarantee no interference in these bands due to higher order harmonics radiation. This effectively enables the user/patient not to interrupt the implant communication in the case of a phone call. The simultaneous communication feature without interruption is a significant concern in implant devices that require continuous and seamless information flow. Link-ICC 540 shown in FIG. 4 can as well be integrated into the cell-phone SOCC 550 shown in the same FIG. 4 to reduce the system cost.

Link-ICC 540 (FIGS. 5 & 6) can be programmed to work in any of the RF-ID bands specified in international Organization for Standardization (ISO14443, ISO15693, ISO18000, etc.) and EPC Global (Class0, Class1, UHF Generation 2, etc.). A fractional phase locked loop (Fractional PLL) 541 inside Link-ICC 540 can be programmed to generate the any of the carrier signals required by these standards (125 KHz-135 KHz band, 13.56 MHz, UHF 900 MHz etc.) from the on-board available crystal frequency reference source 580 with the desired channel characteristics. The output of PLL 541 is first filtered through a filter block 546 to remove the undesired harmonics that may fall into the cellular or other wireless application bands. Fully differential operation, harmonic filtering 542, synchronous wired inductive link through EU-cord 400 all result in a robust interference free communication system which results in simultaneous reception in the cellular bands.

Link-ICC 540 (FIGS. 5 & 6), following the filter 542 is a power amplifier (PA) 543 that drives the primary patch coil 333 at the end of the connecting cable EU-cord 400. The same coil 333 is as well used as a receive path from the implant. The digital data from sensors 331 of the implant modulate 310 the voltage waveform at the primary side 333 by shorting the secondary coil 321 in the implant. This effectively changes the impedance seen in the outside primary side and hence the voltage swing across it changes as well. The modulated waveform in the Link-ICC 540 goes through a receive chain to demodulate and decode the data. The chain includes a programmable attenuator 544, a limiting amplifier 544' to recreate the carrier signal for mixing 545, filters 545 and variable gain amplifiers (VGAs) 546 for signal conditioning, and ADC 547 for conversion to digital and finally a DSP and control logic 548 to extract the data. This final block stores the data and presents it to the cell-phone application processor 550/560 through a standard inter-chip communication interface 549 such as I2C, UART, SPI, and Transport Stream etc. Based on the software the data is stored and processed for the desired user/patient-interface application. Any software calibration can be implemented in this application processor to filter out the sensor irregularities, nonlinearities.

In the secondary implant side 320 shown in FIGS. 7a&7b and FIGS. 5&6, a similar receive chain can be implemented to transfer data to the implant 310 to control actuators 337 handling drug delivery, neural stimulation, and physical organ functions. The receiver 340" again mixes down, filters and conditions the signal that is modulated by the PA 543 of the Link-ICC 540 in the mobile device 500. Then the signal goes into an ADC 547 through a multiplexer that enables the reuse of the ADC for converting the various sensor data into digital domain.

In addition to transmit 340' and receive 340" link circuitries, a rectifier circuit extracts DC power from the received AC signal. So, the sensor data to be transmitted is encoded first to assure frequent high-bit cycles not to cause drop at the rectifier output due to shorting of the secondary implant coil during low-bit cycles. If a large amount of power is required in the implant for any reason then the modulation index can be adjusted by increasing the shorting switch impedance to maintain a minimum supply level at the implant. The modulation index is the ratio of amplitude variation to the signal amplitude itself. The increases in the impedance of the shorting switch causes less variation in the impedance seen on the primary side and hence less variation in the amplitude of the transmitted RF tone.

Though these numerous details of the disclosed devices are set forth here, such as the various components, to provide an understanding of the present invention, it will be obvious, however, to those skilled in the art that these specific details need not be employed to practice the present invention. At the same time, it will be evident that the same methods may be employed in other similar process steps that are too many to cite, such as switching between the functions of a normal mobile phone and a medical monitoring device, or both modes operating simultaneously within the disclosed integrated system environment. That is, with the switch of software application from a drop-down menu, the mobile device of the system can function both as a normal mobile phone, as a medical monitoring device, or both without any interference between the tow modes of operations.

Specifically, in operational mode for the disclosed first architecture, the following steps are followed:
1. Place the Link-ICC 540 in the mobile phone 500 configured to receive the Link-ICC 540, as described above;
2. plug the phone-end 450 of the EU-cord corresponding to the first architecture comprising a two-way near field inductive data/power transfer two-wire cable capable of carrying modulated RF data into any one of the available ports 510, 520, 530 on the mobile phone;
3. adhere the sticky patch 330 at the implant-end 425 of the EU-cord 400 proximate the implant device 310 on the body of the patient 300;
4. Click on the drop-down menu (not shown) in the mobile phone 500 to choose between operating as
   a) An integrated system functioning both as a mobile phone and a medical monitoring device simultaneously; or
   b) as a stand-alone medical monitoring device; or
   c) a mobile phone.

Or, in operational mode for the disclosed second architecture, the following steps are followed:
1. Place the Link-ICC 540 on the outer portion of the sticky patch 330 of the EU-cord 400 corresponding to the second architecture comprising standard power/accessory cable including digital interface wires and power supply wires;
2. plug the phone-end 450 of the EU-cord 400 to the power/accessory port 510 of a generic mobile phone 500;
3. adhere the sticky patch 330 on the implant-end 425 of the EU-cord 400 proximate the implant device 310 on the body of the patient 300;
4. Click on the drop-down menu (not shown) in the mobile phone 500 to choose between operating as
   a) an integrated system functioning both as a mobile phone and a medical monitoring device simultaneously; or
   b) as a stand-alone medical monitoring device; or
   c) a mobile phone.

It will be appreciated that although the disclosed systems in either architectural form may be used in any one of the three modes above, its normal mode of operation would be as an integrated system functioning both as a mobile phone and a medical monitoring device simultaneously. It will also be appreciated that the disclosed systems comprise mobile multimedia or communication devices that are reconfigured in novel ways to serve as a medical device with a custom Link- IC design obviating the need for any other external device except for a new and novel umbilical cord.

While the invention has been particularly shown and described with reference to particular embodiment(s), it will be appreciated that variations of the above-disclosed embodiment(s) and other features and functions, or alternative thereof may be desirably combined into many other different systems or applications. Also that various presently unforeseen or unanticipated alternative, modifications, variations or improvements therein may be subsequently made by those skilled in the art which are also intended to be encompassed by the following claims.

What is claimed is:

1. An integrated mobile device and medical implant system comprising
  a first architecture further comprising;
  a mobile electronic device integrated with an implantable device in the body of a user/patient through an electronic umbilical cord having an implant-end implanted with said implementable device, and a phone-end attachable to said mobile electronic device;
  said implantable device comprising an implant coil and an implant IC hermetically sealed within a substrate;
  said electronic umbilical cord providing inductive communications link between said implantable device and said mobile electronic device through a patch coil affixed to said implant-end patch;
  said implant-end patch further comprising an outer portion configured to receive a Link-ICC acting as an interface between said electronic device and said implantable device through said electronic umbilical cord;
  said umbilical cord further comprising a two-way near field inductive data/power transfer two-wire cable capable of carrying modulated RF data;
  a Link-ICC formed in said mobile phone between a communication port and system-on-chip chip (SOCC), or inside said SOCC, or inside application processor (AP), and capable of acting as an interface between said mobile electronic device and said implantable device through said electronic umbilical cord;
  wherein said Link-ICC is programmable to work in an RF-ID band to generate a carrier signal for fully differential operation for interference-free communication with said implantable device through said electronic umbilical cord, and further configured to have a power amplifier that drives said primary patch coil at said phone-end of said electronic umbilical cord, and a receive chain including a programmable attenuator, a limiting amplifier to recreate a carrier signal for mixing, filters and variable gain amplifiers (VGAs) for signal conditioning, and ADC for conversion to digital signal, a digital signal processor and control logic to extract data from said implantable device, a mobile electronic device interface to present said data to mobile electronic device application processor;
  a mobile electronic device display to present the processed data to the immediate user/patient and/or an antenna to communicate the data wirelessly to a remote location; and
  wherein, said electronic mobile device is capable of functioning both as a normal mobile phone, as a medical monitoring device, or both simultaneously, without any interference between the two modes of operations, with the switch of software application from a drop-down menu inside said mobile phone.

2. The integrated mobile device and medical implant system according to claim 1, wherein said mobile phone is capable of sharing its resources, including display, battery, communication and accessory ports, application processor, crystal oscillator, audio, vibratory and memory to form a complete medical monitoring interface to the user/patient.

3. The integrated mobile device and medical implant system according to claim 1, wherein said implantable device includes biosensors and actuators.

4. The integrated mobile device and medical implant system according to claim 1, wherein said implant-end patch of said electronic umbilical cord is adhesively secured over said implantable device on the body of said user/patient.

5. The integrated mobile device and medical implant system according to claim 1, wherein said phone-end plug of said electronic umbilical cord connects to an audio jack of said mobile phone.

6. The integrated mobile device and medical implant system according to claim 1, wherein said phone-end plug of said electronic umbilical cord connects to any available port on said mobile phone.

7. An integrated mobile device and medical implant system comprising
  a second architecture further comprising;
  a generic mobile phone;
  said generic mobile phone integrated with an implantable device through an electronic umbilical cord having an implant-end implanted with said implementable device, and a phone-end attachable to said mobile phone;
  said electronic umbilical cord having an implant-end patch and a phone-end plug, said electronic umbilical cord comprising standard power/accessory cable including digital interface wires and power supply wires;
  said implant-end patch further comprising an outer portion configured to receive a Link-ICC acting as an interface between said mobile phone and said implantable device through said electronic umbilical cord;
  wherein said Link-ICC is programmable to work in an RF-ID band to generate a carrier signal for fully differential operation for interference-free communication while connected to said mobile phone through said electronic umbilical cord, and further configured to have a receive chain including a programmable attenuator, a limiting amplifier to recreate a carrier signal for mixing, filters and variable gain amplifiers (VGAs) for signal conditioning, and ADC for conversion to digital signal, a digital signal processor and control logic to extract data from said implantable device, a mobile phone interface to present said data to mobile phone application processor;
  a generic mobile phone display to present processed data to the immediate user/patient and/or an antenna to communicate the data wirelessly to a remote location and
  wherein, said electronic mobile device is capable of functioning both as a normal mobile phone, as a medical monitoring device, or both simultaneously, without any interference between the two modes of operations, with the switch of software application from a drop-down menu inside said mobile phone.

8. The integrated mobile device and medical implant system according to claim 7, wherein said mobile phone is capable of sharing its resources, including display, battery, communication and accessory ports, application processor, crystal oscillator, audio, vibratory and memory to form a complete medical monitoring interface to the user/patient.

9. The integrated mobile device and medical implant system according to claim 7, wherein said implantable device includes biosensors and actuators, 10. The integrated mobile device and medical implant system according to claim 7 wherein said implant-end patch, comprising said outer portion, of said electronic umbilical cord is adhesively secured over said implantable device on the body of said user/patient.

11. The integrated mobile device and medical implant system according to claim 7, wherein said phone-end of said electronic umbilical cord connects to power and accessory ports of said mobile phone.

12. The integrated mobile device and medical implant system according to claim 7, wherein said phone-end of said electronic umbilical cord has access to a battery of said mobile phone.

13. A method comprising
providing a first architecture having a mobile phone configured to receive an interface Link-ICC and an implantable medical device communicating through said interface Link-ICC via an electronic umbilical cord having an implant-end patch and a phone-end plug, said implantable device comprising an inductive implant coil, implant IC and biosensors sealed within a substrate;
placing a patch coil on said implant-end patch of said electronic umbilical cord;
placing said Link-ICC inside said mobile phone between a communication port and system-on-chip chip (SOCC), or inside said SOCC, or inside application processor (AP);
securing adhesively said implant-end patch of said electronic umbilical cord onto the body of said user/patient over said implantable medical device;
connecting said phone-end of said electronic umbilical cord further comprising a two-way near field inductive data/power transfer two-wire cable capable of carrying modulated RF data to said mobile phone;
turning on said mobile phone having a battery;
clicking on the drop-down menu of said mobile phone to choose between multiple of modes operation;
said modes of operation comprising at least functioning as a mobile phone and a medical monitoring device simultaneously, or as a stand-alone medical monitoring device, or as a standard mobile phone;
transceiving data to and fro said implantable medical device; and
presenting processed data in a useful format to the user/patient and/or transmit wirelessly to a remote location.

14. The method according to claim 13, wherein receiving medical data from said implantable device is accomplished by plugging said phone-end of said electronic umbilical cord to audio jack of said mobile phone while not interfering with normal communications functionality of said mobile phone.

15. The method according to claim 13, wherein said wireless transmission of data is accomplished by storing sensory data received from said implantable device in said mobile device memory and sending said data using normal mobile phone functions.

16. A method comprising providing a second architecture having a generic mobile phone and an implantable medical device communicating through an interface Link-IC via an electronic umbilical cord having an implant-end patch and a phone-end plug, said implant-end patch having an outer portion, said implantable medical device comprising an inductive implant coil, implant IC and biosensors sealed within a substrate;
placing an inductive patch coil on said implant-end patch of said electronic umbilical cord;
placing said Link-ICC on said outer portion of said implant-end patch of said electronic umbilical cord;
enabling said Link-ICC to affect power/data transfer with said implantable device through said inductive patch coil and inductive implant coil;
securing adhesively said implant-end patch of said electronic umbilical cord onto the body of said user/patient over said implantable medical device;
connecting said phone-end of said electronic umbilical cord further comprising standard power accessory cable which contains standard digital data communication wires and power supply lines;
turning on said mobile phone having a battery;
clicking on the drop-down menu of said mobile phone to choose between multiple of modes operation;
said modes of operation comprising at least functioning as a mobile phone and a medical monitoring device simultaneously, or as a stand-alone medical monitoring device, or as a standard mobile phone.
transceiving data to and fro said implantable medical device; and
presenting processed data in a useful format to the user/patient and/or transmit wirelessly to a remote location.

17. The method according to claim 16, wherein receiving medical data from said implantable medical device is accomplished by plugging said phone-end of said electronic umbilical cord to power/accessory port of said mobile phone while not interfering with normal communications functionality of said mobile phone.

18. The method according to claim 16, wherein said wireless transmission of data is accomplished by storing sensory data received from said implantable device in said mobile device memory and sending said data using normal mobile phone functions.

19. he integrated mobile device and medical implant system according to claim 1, wherein said integrated mobile device comprises a mobile multimedia or communication device reconfigured to serve as a medical device with a custom Link-IC design obviating the need for any other external device except for said umbilical cord.

* * * * *